United States Patent [19]

Jones

[11] Patent Number: 4,685,912
[45] Date of Patent: Aug. 11, 1987

[54] I.V. DRIP CHAMBER WITH BUILT-IN PUMP ACTIVATED BY EXTERNAL MEANS
[75] Inventor: J. Paul Jones, Glenmoore, Pa.
[73] Assignee: Patent Research and Development Corp., Exton, Pa.
[21] Appl. No.: 836,503
[22] Filed: Mar. 5, 1986
[51] Int. Cl.⁴ .............................................. A61M 5/14
[52] U.S. Cl. .................................... 604/247; 604/65; 604/251; 128/DIG. 12
[58] Field of Search .................................. 604/51–53, 604/65, 8–9, 185, 246, 247, 251; 128/DIG. 12

[56] References Cited
U.S. PATENT DOCUMENTS

| | | | |
|---|---|---|---|
| 2,208,032 | 7/1940 | Hooper | 604/246 |
| 2,907,325 | 10/1959 | Burke | 604/185 |
| 2,989,052 | 6/1961 | Broman | 604/185 |
| 3,021,841 | 2/1962 | Burke | 604/185 |
| 3,527,226 | 9/1970 | Hakim | 604/247 |
| 3,664,339 | 5/1972 | Santomieri | 604/188 |
| 3,683,929 | 8/1972 | Holter | 604/247 |
| 3,832,999 | 9/1974 | Crilly | 604/185 |
| 4,038,983 | 8/1977 | Mittleman et al. | 604/185 |
| 4,332,255 | 6/1982 | Hakim et al. | 604/247 |
| 4,409,991 | 10/1983 | Eldridge | 604/246 |

Primary Examiner—C. Fred Rosenbaum
Assistant Examiner—Sherri Vinyard
Attorney, Agent, or Firm—Frederick J. Olsson

[57] ABSTRACT

A flexible tube is mounted on top of thé drip chamber. The top of the tube is connected to the spike via a one-way ball-type valve. The bottom of the tube is connected to the drip chamber via a duck-bill-type valve inside of the drip chamber. The duck-bill is held closed against head pressure by a metal spring clip acting on the lip. The duck-bill will open when the tube is squeezed and fluid will be injected into the drip chamber.

The drip chamber is charged bubble-free by the use of an output tube open to the chamber and joined to the flexible tubing carrying the hypodermic needle. During the initial fill the output tube is positioned above the fluid level and air in the chamber vented via the output tube, the flexible tubing and the hypodermic needle. When the desired level is reached, the output tube is submerged and bubble-free fluid fills the output tube, the flexible tubing, and the hypodermic needle.

3 Claims, 4 Drawing Figures

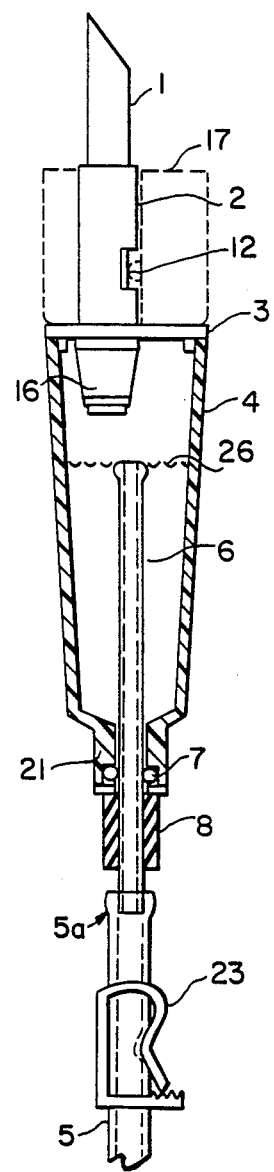
FIG. IA
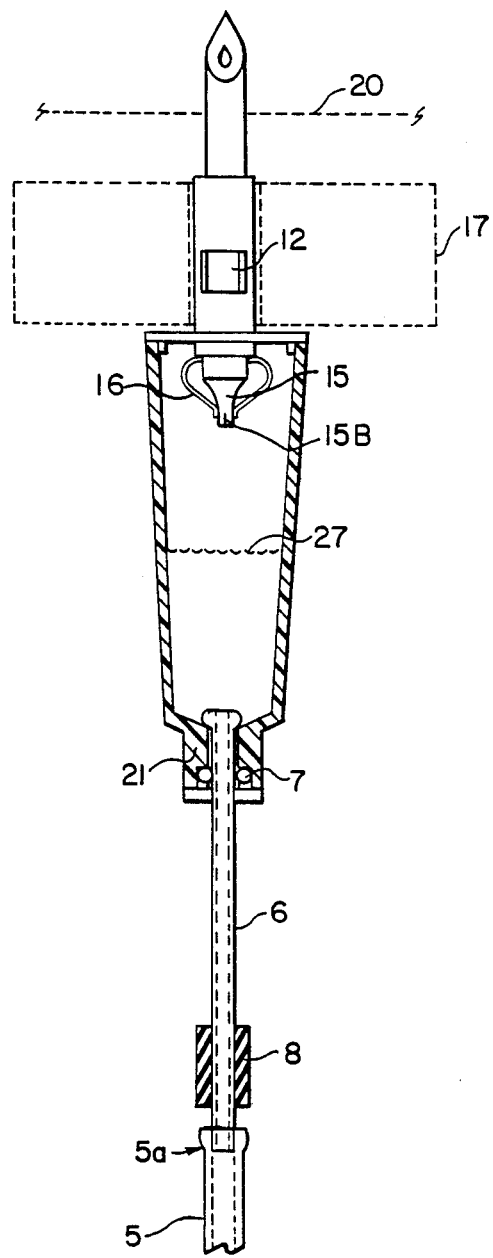
FIG. IB

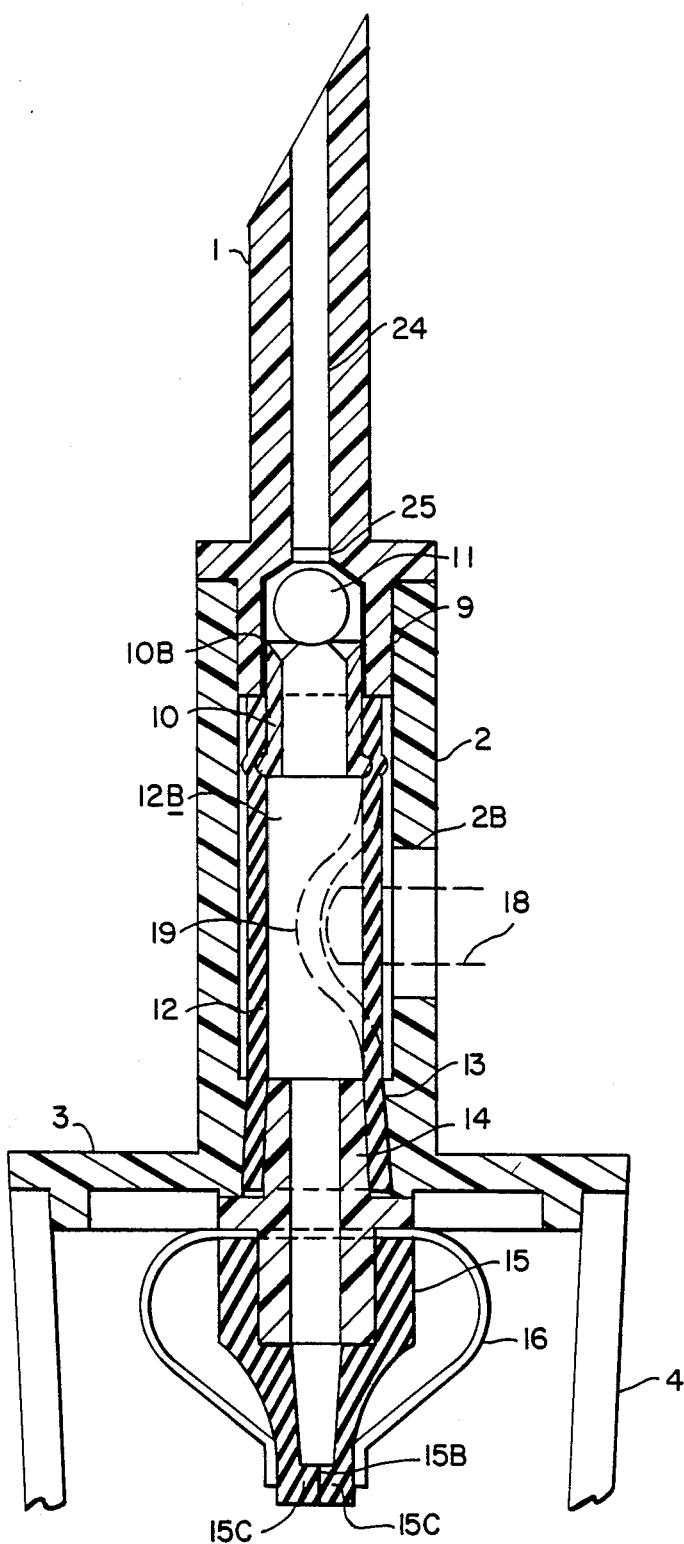
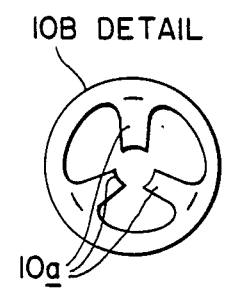
FIG. 2B
FIG. 2A

I.V. DRIP CHAMBER WITH BUILT-IN PUMP ACTIVATED BY EXTERNAL MEANS

This invention relates in general to drip chambers for intravenous infusion systems and in particular relates to a pump for injecting drops into the drip chamber and to a method and means for making the initial fill of the chamber, PVC tubing, and hypodermic needle bubble free.

Ordinary intravenous I.V. infusion sets are basically made up of three parts: (1) a spike which is inserted in the bottom of a suspended fluid source; (2) a cylindrical transparent drip chamber which receives the drops from a small aperture in the spike; and (3) a length of flexible PVC tubing which connects the drip chamber to the needle which is inserted into the vein of the patient. There is, in addition, a variable clamp on the PVC tubing which squeezes the tubing to cause a constriction in the fluid flow.

As simple as these basic elements may seem, there is a complicated interrelation between: (1) the height of the "head" of the fluid source above the drop aperture; (2) the size of the drop aperture; (3) the amount of low pressure or suction initially set up by the fluid level in the chamber; (4) the total height of the drip chamber above the patient which determines the syphon effect of the fluid in the tubing; and (5) the resistance to the flow set up by the constricting clamp on the PVC tubing.

All of these factors in combination, or any one of them alone, can affect the drop rate into the chamber and/or the size of the drop. To make matters worse, the drop size and rate can also be affected by the viscosity and temperature of some fluids.

Perhaps the most troublesome of the listed variables is the conventional adjustment clamp which can change its setting as much as 100% in 15 minutes because of the slow rate of change of the set in the PVC tubing when the clamp is tightened or loosened. There are more precision constricting valves which are made to be inserted in series with the tubing. These series control valves can add some precision for additional cost, but all of the other variables mentioned still remain.

It is, therefore, one object of this invention to provide an inexpensive drip chamber which can be controlled with a small clip-on actuator and which, by its design, can set the exact rate of fluid flow (i.e. drop size and rate) while eliminating the variables of: (1) fluid head height; (2) drop aperture; (3) setting up fluid level; (4) the effect of chamber height; and (5) the instability of the variable clamp. The danger of "flow through" (i.e. when all of the fluid runs out of the tube carrying air into the patient's vein) which can occur in the design of some controllers, is eliminated by the invention since the impulse pump on the drip chamber is normally cut off between electrical impulses from the associated control unit.

Another undesirable characteristic of conventional I.V. systems is that of making the initial fill of the drip chamber and connected PVC tubing and hypodermic needle bubble-free so air cannot be injected into the patient. It is another object of the invention to provide a method and means for a bubble-free initial fill.

The invention will be described below in connection with the following drawings wherein:

FIG. 1A is an elevational view partially in section illustrating an intervenous infusion system drip chamber incorporating my invention;

FIG. 1B is another elevational veiw partially in section of the drip chamber of FIG. 1A;

FIG. 2A is an enlarged fragmentary view of the top part of FIG. 1A and illustrating drip pump; and FIG. 2B is a plan view of a component of the pump of FIG. 2A.

With reference to FIGS. 1A and 1B, the impulse controlled drip chamber (4) is shown actual size with the dotted lines showing the approximate size of the associated impulse actuator (17) which clamps on to the top of the drip chamber assembly around the square periphery of a hollow rigid extension (2). The impulse actuator (17) is, therefore, no larger than the drip chamber itself, and is located just under the fluid source (20); and is entirely supported by the chamber.

The spike (1) is used to pierce the elastomer seal on the fluid source (20), and the frictional fit will easily support the entire drip chamber assembly and impulse actuator (17).

The spike (1) is welded into the square extension (2) and is connected to the top section (3) of the drip chamber.

There is a vertically movable output tube (6) which is normally extended into the drip chamber (4) until stopped by an abutment in the form of the elastomer finger grip (8) or in the form of the enlarged head 5a. The height that the output tube (6) extends initially into the drip chamber (4) determines the initial fill height of the fluid (26) and the stem (6) is designed to release the air pressure build-up in the chamber (4) while it is initially being filled with fluid to its top level (26) as shown in FIG. 1A. The release of air is through the tube (6), the flexible tubing (5), and the hypodermic needle (not shown) connected thereto.

In FIG. 1B the output tube (6), which is sealed by the O-ring (7), has been drawn down to the bottom of the chamber (21) which allows the output tube (6), the flexible tube (5), and hypodermic needle to quickly fill, without intermittant breaks or bubbles. When the tubes (5) and (6) have been fully filled and fluid is running out of the hypodermic needle, the fluid in the chamber (4) will be stabilized to the new lower level (27) because of the partial vavuum (suction) created by the weight of the water column in the tubes (5) and (6). Then the auxillary cut-off clamp (23) can be used to totally fix the fluid in the tubes (5) and (6) and injection of hypodermic needle until the needle is inserted into the patient. The fluid in the tubes (5) and (6) and in the hypodermic needle will be without bubbles.

This simple set-up procedure is designed to circumvent a presently tedious set-up process which requires trained I.V. crews. The new invention is designed to make the use of the chambr "fool proof" enough to be used by non-specialist attendants in both hospital and home care environments.

With reference to the expanded drawing, FIG. 2A, the spike (1) has a fluid aperture or passageway (24) which has a small spherical valve seat (25) that mates with a plastic ball valve (11). This ball in practice is 0.125 inches in diameter. The spike base (9) has a small cylindrical insert (10) which has a valve aperture pattern (see FIG. 2B) which allows the fluid to pass, but has fingers (10a) which retain the plastic ball valve (11) loosely, with a 0.015 gap from the valve seat (25). The insert (10) is hollow and forms part of the passageway (24).

An elastomer tube (12) is frictionally retained on the spike insert (10) at the top, and is pressure-sealed at the bottom end by the valve plug (14) in the aperture (13) of the top plate (3). This tube (12) thereby forms a sealed inner chamber 12b that is terminated by a "duck bill" type check valve (15) at the bottom which is retained by friction on the valve plug (14). The duck bill valve (15) has an exit slot ((15B) which forms the valve opening.

A spring stainless steel pressure clip (16) maintains closing pressure (i.e. enough to resist the maximum fluid head pressure above) on the lips (15C) of the valve opening (15B). The combination of the plastic elastomer valve (15) and external pressure clip (16) provides a unique valve, with unfatigable pressure provided by the metal spring clip which in turn is not exposed to the fluid inpassage. This feature is an important part of the invention.

Notice that the elastomer tube (12) is shown in a position by dotted lines (19) wherein it has been depressed by an external actuator or probe (18) that is allowed to enter through the wall of the outer cylinder (2) through the aperture (2B).

It has been found that the uniform depression of the tube in terms of depth and width of the probe (18) displaces a very uniform volume of fluid in the tube (12 which is relatively independent of such production variables as the tube wall thickness, tube length, etc.

As soon as the probe (18) begins to depress the tube wall to the position (19) part of the fluid in the tube moves up to cause the plastic ball valve (11) to instantly rest against the valve seat (25) and prevent any upward flow of the displaced volume of fluid. The otherpart of fluid displaced by the tube at position (19) can only go out the check valve (15) by overcoming the holding pressure of the spring clip (16). It will be apparent that each time the probe or actuator (18) is operated the same volume of fluid is passed through the check valve (15) to the drip chamber.

When the probe (18) is retracted, the elastomer (for example silicone) tube quickly resets to its normal round shape, thereby allowing new fluid to flow down through the ball valve (11) aided by the head pressure from the fluid source above.

The pumping action has thereby been added to a relatively standard I.V. drip chamber with only four small and inexpensive parts. These extra parts include the plastic ball (11), the small section of elastomer tubing (12), the elastomer check valve (15), and the check valve clip spring (16). As is conventional in I.V. systems, all of the parts are plastic (so as to avoid metal contact with the fluid) except the spring clip (16) which is metal but not contactable by the fluid in the check valve (15) nor the fluid exiting through opening (15B).

Before closing I want to point out several important characteristics of the invention. This is done in paragraphs (A) through (G) below.

(A)

A drip chamber including a cap on the top thereof which has a hollow cylindrical extension and a tapered hole in the cap to receive the lower end of the contained section of flexible tubing and a tapered compression plug; a connection spike with a center aperture which is fused to the top of the hollow cylindrical extension and is used to pierce the seal of the fluid source; a plastic ball located below a conforming seat around the edge of the center aperture at the base of the connection spike; a hollow plug which has radial extensions at the top that limit the vertical travel of the plastic ball when the plug is mounted in a hollow cylindrical extension at the base of the spike; a section of flexible tubing which is compression mounted at the top end on an extension of the hollow plug and has its lower end compression sealed by the tapered compression plug; a flexible "duck bill"-type output check valve which is mounted on a tubular extension of the compression plug in the chamber cap; a metallic spring clip which is retained by the mounting of the flexible check valve and has opposing fingers which press against opposite sides of the valve lips to control the release pressure of the valve.

(B)

An aperture in the side of the hollow cylindrical extension of the drip chamber cap which exposes the centrally located section of flexible tubing which conducts the I.V. fluid from the spike aperture, past the ball valve, and down to the pressure controlled output check valve.

(C)

An aperture in the side of the cylindrical extension of the drip chamber cap admits a reciprocating finger that compresses the contained section of flexible tubing to eject a measured amount of fluid through the pressure controlled output check valve such reciprocating finger being driven by an external means that is normally off and provides a single reciprocating motion for each control impulse applied.

(D)

The spring clip on the flexible output check valve has the design feature of being presettable to a pressure level that will overcome the maximum vertical head pressure from the fluid source and the additional feature of not being exposed to the I.V. fluid that is passing through the output check valve, the pressure setting being established by the thickness of the metal used in the pear-shaped design of the clip and/or the tension formed into the gap between the clip ends before the lips of the flexible check valve are inserted.

(E)

A concentric space around the section of flexible tubing located within the hollow extension of the drip chamber cap is made large enough to allow the flexible tubing to freely expand in width when it is compressed and deformed by the reciprocating finger from an external actuation means such free expansion space being necessary to keep the volume of fluid displaced by the actuator regulated primarily by the uniform size and movement of the actuator finger and not seriously affected by small variations of the outside O.D. of the flexible tubing.

(F)

The design and assembly method of the tapered compression plug in the bottom of the section of flexible tubing and the tapered hole in the cap of the drip chamber mounts the flexible tubing in a condition of mild compression between its two ends, such compression overcoming any tendency for the flexible tubing to move on the hollow plug extension at the base of the spike or in the compression fitting in the cap of the chamber when the flexible tubing is being deformed by the actuator finger extending through the aperture in the side of the hollow cylindrical extension of the chamber cap.

(G)

A vertically movable output tube in the O-ring sealed base of the drip chamber which is connected to the I.V. tubing to the needle and which is designed to such a length that when fully inserted into the chamber at the start of filling, it allows the trapped air to escape from the non-vented chamber and gauges the amount of fluid that should be initially moved into the chamber by a rapid fill control, such gauged fluid level also calculated to rapidly fill the I.V. tube to the needle with fluid without trapped air bubbles when the constrained tube is moved downward to the bottom of the initial fluid level in the chamber with the final level of fluid in the chamber being established by the filling of the I.V. tube and the resulting partial vacuum in the chamber which will prevent excess fluid form running out of the I.V. tubing (called feed-through) when the insertion of controlled drops is stopped.

I claim:

1. In an intervenous infusion system, the combination of:
   a source of fluid;
   spike means having a fluid entrance passageway, the spike means being connected to said source to receive fluid therefrom;
   means forming a hollow drip chamber to receive fluid from said spike means, the chamber having a top section and a bottom section;
   a flexible tube to pass fluid from said spike to said drip chamber;
   means including a one-way ball valve connecting one end of said flexible tube to said spike means, the one-way ball valve having an open condition where fluid can pass from said fluid entrance passageway into the flexible tube and a closed condition wherein passage of fluid therethrough is prevented;
   means including a duck-bill valve connecting the opposite end of said flexible tube adjacent the top section of said drip chamber with the flexible tube extending away from the drip chamber and the duck-bill valve including a slit having an open condition wherein fluid can pass therethrough from the flexible tube into the drip chamber and a closed condition wherein passage of fluid therethrough is prevented;
   spring means made of metal inside said drip chamber and engaging said duck-bill valve and exerting a closure force urging said slit to the closed condition and the spring means being disposed exterior to the duck-bill valve to avoid contact with fluid inside the valve and with fluid exiting from the slit;
   means disposed between said valves and spaced from but positioned with respect to one side of said flexible tube to be interengaged therewith and support the one side when the opposite side of the tube is engaged by an actuator which operates to push the opposite side toward the one side and displace the fluid in the tube, one portion of the displaced fluid moving toward said one-way valve to cause the ball to close the valve and another portion of the displaced fluid moving toward said duck-bill valve to open said slit whereby a quantity of fluid enters said drip chamber;
   the magnitude of said force generated by said spring means being great enough to maintain said closed condition against the head pressure of the fluid between said slit and said source and low enough so that the pressure of said displaced fluid causes the slit to assume said open condition; and
   said spike means, said drip chamber, said flexible tube, said one-way valve, said duck-bill valve, all being formed of plastic material.

2. For an intervenous infusion system, the combination of:
   means forming a hollow drip chamber having a top section and a bottom section, the top section having an opening by which fluid is passed into the chamber;
   an elongated, flexible tube to pass fluid;
   mounting means mounting one end of said flexible tube around said opening and to extend outwardly of the top section, the mounting means including a first passageway open to the tube;
   a duck-bill valve disposed inside of said drip chamber and connected to said mounting means and open to said first passageway, the duck-bill valve having a slit section having an open condition wherein fluid can pass therethrough into the drip chamber and a closed condition wherein passage of fluid is prevented;
   spring means made of metal inside of said drip chamber and engaging said duck-bill valve and exerting a closure force urging said slit to the closed condition, the spring means being disposed exterior to the duck-bill valve to avoid contact with fluid inside of the duck-bill valve and with fluid exiting from the slit;
   a hollow, rigid, elongated extension connected to the top section of said drip chamber and surrounding and spaced from said flexible tube, the extension having at least one opening in communication with the flexible tube for use in permitting an actuator to enter the opening and move through said space to engage the flexible tube;
   spike means mounted on said extension and including a second fluid passageway and the opposite end of said flexible tube being mounted on said spike means and open to said second fluid passageway;
   one-way ball valve means formed in said second fluid passageway and having an open condition for passing fluid through the second fluid passageway into said flexible tube and a closed condition preventing fluid flowing from said flexible tube through said second fluid passageway; and
   said drip chamber, said flexible tube, said mounting means, said duck-bill valve, said elongated extension, said spike means, and said one-way valve means all being made of plastic material to avoid fluid contacting metal.

3. For an intervenous infusion system, the combination of:
   means forming a hollow drip chamber having a top section and a bottom section, the top section having an opening by which fluid is passed into the chamber;
   an elongated output tube movable along its axis to a vent position wherein the tube carries air and to an operating position wherein the tube carries fluid;
   an opening formed in said bottom section and having support means slidably mounting said output tube whereby part of the tube extends inside of the drip chamber and part of the tube extends outside of the drip chamber, the support means including an O-ring surrounding the output tube to permit sliding motion and forming a fluid seal, the end of the tube inside of the drip chamber being of greater diameter than said opening and forming a first abutment to engage the inside of the drip chamber around the opening to prevent the output tube from moving out of the opening, the engagement establishing said operating position of the output tube; and a second abutment on the portion of the output tube exterior to the drip chamber to engage said bottom section of the drip chamber when the output tube is moved toward the interior of the chamber, the engagement establishing said vent position of the output tube.

* * * * *